US012629160B2

(12) United States Patent
Chanduszko et al.

(10) Patent No.: US 12,629,160 B2
(45) Date of Patent: May 19, 2026

(54) THROMBECTOMY DEVICES AND METHODS

(71) Applicant: Bard Peripheral Vascular, Inc., Franklin Lakes, NJ (US)

(72) Inventors: Andrzej J. Chanduszko, Chandler, AZ (US); Matthew R. Casiraro, Tempe, AZ (US)

(73) Assignee: Bard Peripheral Vascular, Inc., Franklin Lakes, NJ (US)

( * ) Notice: Subject to any disclaimer, the term of this patent is extended or adjusted under 35 U.S.C. 154(b) by 106 days.

(21) Appl. No.: 18/292,688

(22) PCT Filed: Jan. 9, 2023

(86) PCT No.: PCT/US2023/060316
§ 371 (c)(1),
(2) Date: Jan. 26, 2024

(87) PCT Pub. No.: WO2024/151303
PCT Pub. Date: Jul. 18, 2024

(65) Prior Publication Data
US 2025/0082347 A1 Mar. 13, 2025

(51) Int. Cl.
*A61B 17/22* (2006.01)
*A61M 1/00* (2006.01)

(52) U.S. Cl.
CPC .............. *A61B 17/22* (2013.01); *A61M 1/77* (2021.05); *A61B 2017/22079* (2013.01); *A61B 2017/22084* (2013.01)

(58) Field of Classification Search
CPC .......... A61B 17/22; A61B 2017/22079; A61B 2017/22084; A61M 1/77
See application file for complete search history.

(56) References Cited

U.S. PATENT DOCUMENTS 4,642,833 A 2/1987 Stoltz et al.
5,417,703 A * 5/1995 Brown ........... A61B 17/320783
606/171

(Continued)

FOREIGN PATENT DOCUMENTS

EP 2548601 A1 1/2013

OTHER PUBLICATIONS

International Search Report and Written Opinion dated Jul. 12, 2023, in International Application No. PCT/US2023/060316.

*Primary Examiner* — Julian W Woo
(74) *Attorney, Agent, or Firm* — Dinsmore & Shohl LLP

(57) ABSTRACT
A thrombectomy device for removing a material from a subject includes a catheter, a diaphragm, and a vacuum. The catheter includes an outer body defining a lumen extending therethrough. The diaphragm is coupled to the catheter and is moveable between an open diaphragm configuration and a closed diaphragm configuration. The diaphragm allows movement of the material through the lumen when in the open diaphragm configuration and prevents movement of the material through the lumen when in the closed diaphragm configuration. The vacuum is in communication with the lumen and is operable to exert a vacuum pressure on the diaphragm. The vacuum pressure is operable to move the diaphragm from the open diaphragm configuration to the closed diaphragm configuration.

20 Claims, 6 Drawing Sheets

(56)  References Cited

U.S. PATENT DOCUMENTS

| 7,998,107 | B2 * | 8/2011 | Nash | ..................... | A61M 1/743 |
| | | | | | 604/35 |
| 11,464,528 | B2 * | 10/2022 | Brady | ................... | A61M 1/743 |
| 12,350,417 | B2 * | 7/2025 | Jalgaonkar | ............. | A61B 17/22 |
| 2006/0054229 | A1 | 3/2006 | Van Der Meijden et al. | | |
| 2007/0021774 | A1 | 1/2007 | Hogendijk | | |
| 2014/0259465 | A1 | 9/2014 | Van Der Meijden | | |
| 2019/0365567 | A1 | 12/2019 | Balkenbush et al. | | |
| 2022/0168000 | A1 | 6/2022 | Naglreiter et al. | | |

* cited by examiner

THROMBECTOMY DEVICES AND METHODS

CROSS-REFERENCE TO RELATED APPLICATIONS

This application is a U.S. National Phase of International Application No. PCT/US2023/060316, entitled "Thrombectomy Devices And Methods" and filed Jan. 9, 2023, which is incorporated herein by reference in its entirety.

TECHNICAL FIELD

The present specification generally relates to thrombectomy devices and methods, and, more specifically, interrupted thrombectomy devices and methods.

BACKGROUND

Cardiovascular diseases are a leading cause of death worldwide. Vascular occlusions refer to blockages of blood vessels. Thrombosis is a specific type of vascular occlusion caused by a thrombus (i.e. a blood clot). Thrombi are formed from aggregated platelets, red blood cells, and fibrin proteins, but may also include plaque and other blood-borne substances such as fat, cholesterol, and calcium.

Thrombi can form in both arteries and veins. Venous thrombosis leads to congestion of the affected part of the body, while arterial thrombosis affects the blood supply to tissue and can lead to ischemia or necrosis. Additional complications can arise when a piece of either an arterial or a venous thrombus breaks off. This piece of thrombus, called an embolus, can travel through the circulation and lodge somewhere else as an embolism.

Medical procedures such as thrombectomy can be used to remove thrombi from a blood vessel. One method of thrombectomy is mechanical aspiration. As a thrombus ages, it may become more fibrous and therefore more resistant to aspiration and mechanical fragmentation. This may result in blockages of existing aspiration devices due to a large clot burden. If the thrombectomy device is blocked, the procedure may be extended or an additional device may be required.

Accordingly, a need exists for devices to improve performance of occlusion removal by enhancing aspiration and decreasing the occurrence of blockage of the thrombectomy device.

BRIEF SUMMARY

Embodiments of the present disclosure are directed to thrombectomy devices and methods of using thrombectomy devices with enhanced aspiration to assist in removing material from hollow anatomical structures, such as a vessel or the like. In operation, thrombectomy devices according to the present disclosure generate a vacuum pressure, which aspirates the occlusive material from the vessel through the catheter. In embodiments, thrombectomy devices may generate vacuum pressure intermittently, or cyclically. This may allow the occlusive material to be aspirated through the lumen of the catheter more effectively, thereby preventing blockage or clogging of the catheter according to the present disclosure.

According to one embodiment of the present disclosure, a thrombectomy device for removing a material from a subject includes a catheter, a diaphragm, and a vacuum. The catheter includes an outer body defining a lumen extending therethrough. The diaphragm is coupled to the catheter and is moveable between an open diaphragm configuration and a closed diaphragm configuration. The diaphragm allows movement of the material through the lumen when in the open diaphragm configuration and prevents movement of the material through the lumen when in the closed diaphragm configuration. The vacuum is in communication with the lumen and is operable to exert a vacuum pressure on the diaphragm. The vacuum pressure is operable to move the diaphragm from the open diaphragm configuration to the closed diaphragm configuration.

According to another embodiment of the present disclosure a thrombectomy device for removing a material from a subject includes a catheter, a diaphragm, a vacuum, and a fluid reservoir. The catheter includes an outer body defining a lumen extending therethrough. The diaphragm is disposed within the lumen and is moveable between an open diaphragm configuration and a closed diaphragm configuration. The diaphragm allows movement of the material through the lumen when in the open diaphragm configuration and prevents movement of the material through the lumen when in the closed diaphragm configuration. The vacuum is in communication with the lumen and is operable to exert a vacuum pressure on the diaphragm. The vacuum pressure is operable to move the diaphragm from the open diaphragm configuration to the closed diaphragm configuration. The fluid reservoir assembly is in communication with the lumen and is operable to exert a pressure within the thrombectomy device. The pressure exerted by the fluid reservoir assembly is operable to move the diaphragm from the closed diaphragm configuration to the open diaphragm configuration According to another embodiment of the present disclosure, a method of performing a thrombectomy includes inserting a thrombectomy device into a subject and removing a material from the subject with the thrombectomy device. The thrombectomy device includes a catheter, a diaphragm, and a vacuum. The catheter includes an outer body defining a lumen extending therethrough. The diaphragm is coupled to the catheter and is moveable between an open diaphragm configuration and a closed diaphragm configuration. The diaphragm allows movement of the material through the lumen when in the open diaphragm configuration and prevents movement of the material through the lumen when in the closed diaphragm configuration. The vacuum is in communication with the lumen and is operable to exert a vacuum pressure on the diaphragm. The vacuum pressure is operable to move the diaphragm from the open diaphragm configuration to the closed diaphragm configuration.

Additional features and advantages of the technology disclosed in this disclosure will be set forth in the detailed description which follows, and in part will be readily apparent to those skilled in the art from the description or recognized by practicing the technology as described in this disclosure, including the detailed description which follows, the claims, as well as the appended drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

FIG. 7A at a third time according to one or more embodiments shown and described herein.

DETAILED DESCRIPTION

Embodiments of the present disclosure are generally directed to thrombectomy devices and methods with enhanced aspiration to assist in removing material from hollow anatomical structures, such as a vessel or the like. In operation, thrombectomy devices according to the present disclosure generate a vacuum pressure, which aspirates the occlusive material from the vessel through the catheter. In embodiments, thrombectomy devices may generate vacuum pressure intermittently, or cyclically. This may allow the occlusive material to be aspirated through the lumen of the catheter more effectively, thereby preventing blockage or clogging of the catheter.

These and additional embodiments will be discussed in greater detail with reference to the figures.

Figure 1A:
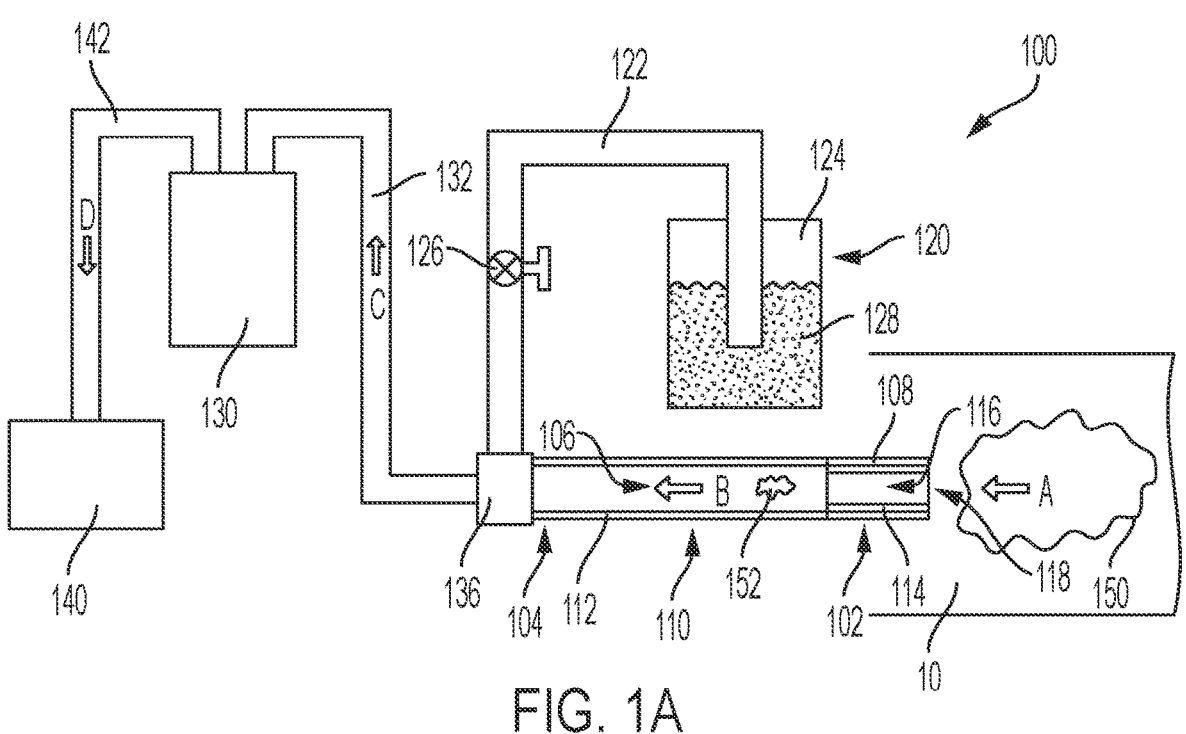
FIG. 1A schematically depicts a diagram of a thrombectomy device having a diaphragm in an open diaphragm configuration, according to one or more embodiments shown and described herein.
Figure 1B:
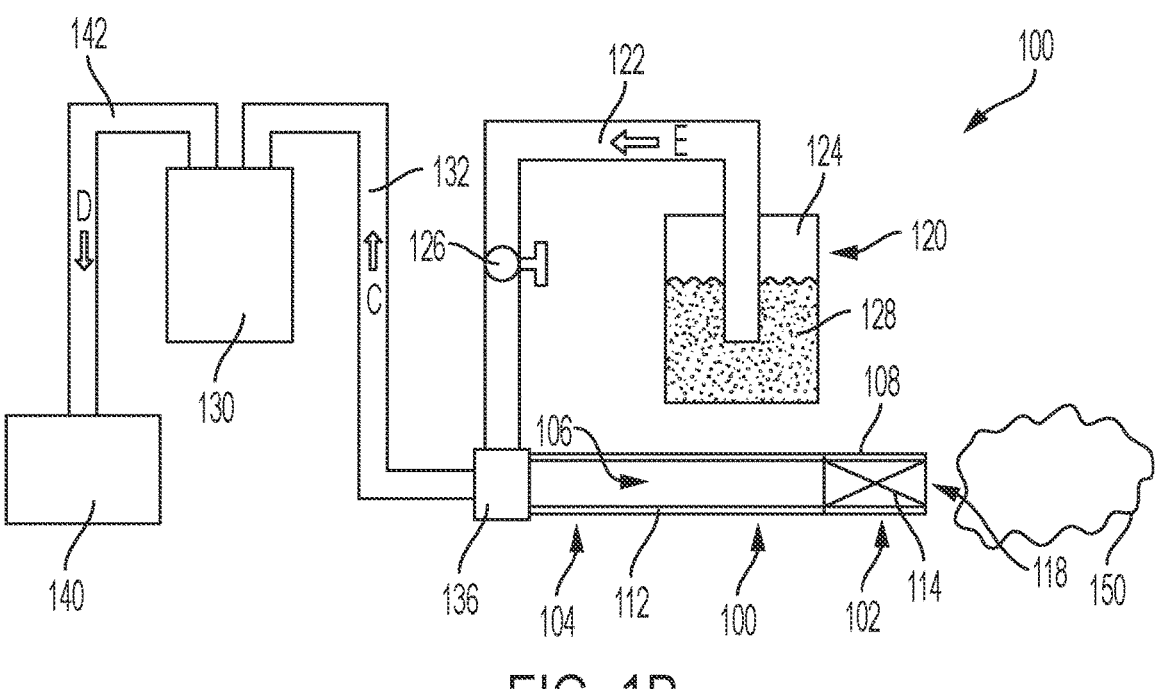
FIG. 1B schematically depicts of the diaphragm of FIG. 1A in a closed diaphragm configuration, according to one or more embodiments shown and described herein.

Now referring to FIGS. 1A and 1B, an embodiment of a thrombectomy device 100 is schematically depicted. In embodiments, the thrombectomy device 100 includes a catheter 110 in communication with a vacuum 140. The vacuum 140 may be a vacuum pump, a suction device, or any other device that is capable of creating a lower pressure within the catheter 110 so as to encourage suction of material into the catheter 110. The catheter 110 may include an outer body 112 that extends between a distal end 102 and a proximal end 104. The outer body 112 may be sized to be advanced axially through a body lumen, such as a blood vessel, or the like. The outer body 112 may be any material suitable for advancing through a vessel, such as, but not limited to, polyurethanes, polyamides, fluoropolymers, polyolefins, PVC, polyimides, polyetheretherketone, or the like.

The catheter 110 may have a distal tip 108 disposed at the distal end 102 of the outer body 112. The distal tip 108 may be generally cylindrical. In some embodiments, the distal tip 108 may taper toward the distal end. Tapering may improve advancement of the catheter 110 through a lumen. The distal tip 108 may be formed integrally with the outer body 112 or coupled thereto. The distal tip 108 may be made from the same or different materials than outer body 112. The distal tip 108 may be any material suitable for advancing through a vessel, such as, but not limited to, metals (stainless steel, titanium, etc.) plastics, or composite materials.

The catheter 110 may define a lumen 106 extending through the outer body 112 and the tip distal 108. The catheter 110 may have an opening 118 in fluid communication with the lumen 106 such that a material 150, e.g., occlusive material (e.g., clot, thrombus, etc.) within a body vessel 10 (e.g., artery, vein, etc.), may be received within the lumen 106 via the opening 118. For example, as depicted, a portion 152 of the material 150 is received within the lumen 106. In embodiments, the opening 118 may be disposed within the distal tip 108. In other embodiments, the opening 118 may be near or adjacent the distal tip 108. For example, the opening 118 may be formed radially in the outer body 112.

As described above, the catheter 110 may be advanced axially through a body lumen, such as a blood vessel, or the like. In some embodiments, a guidewire (not depicted) may be inserted into the blood vessel, and the catheter 110 may be inserted into the blood vessel over the guidewire. In other embodiments, a guidewire may not be included.

Still referring to FIGS. 1A and 1B, the catheter 110 may also include a diaphragm 114 moveable between an open diaphragm configuration (FIG. 1A) and a closed diaphragm configuration (FIG. 1B). In embodiments, the diaphragm 114 may be substantially cylindrically shaped to match an axial cross-sectional shape of the lumen 106, though other shapes are contemplated and possible. The diaphragm 114 may be disposed at the distal end 102 of the outer body 112. In some embodiments, the diaphragm 114 may be disposed within the distal tip 108, such as depicted. In other embodiments, the diaphragm 114 may be disposed within the lumen 160, adjacent or spaced apart from the distal tip 108.

When in the open diaphragm configuration, such as depicted in FIG. 1A, the diaphragm 114 may define a diaphragm passage 116 through which the material 150 may pass. Accordingly, when the diaphragm 114 is in the open diaphragm configuration, the material 150 may be received through the opening 118 of the catheter 110, may pass through the diaphragm passage 116, and may move through the lumen 106. When in the closed diaphragm configuration, such as depicted in FIG. 1B, the diaphragm 114 may be completely or substantially closed such that the material 150 may not pass through the diaphragm passage 116. Accordingly, when the diaphragm 114 is in the closed diaphragm configuration, the material 150 may be prevented from moving through the lumen 106.

Figures 2, 3A, 3B:
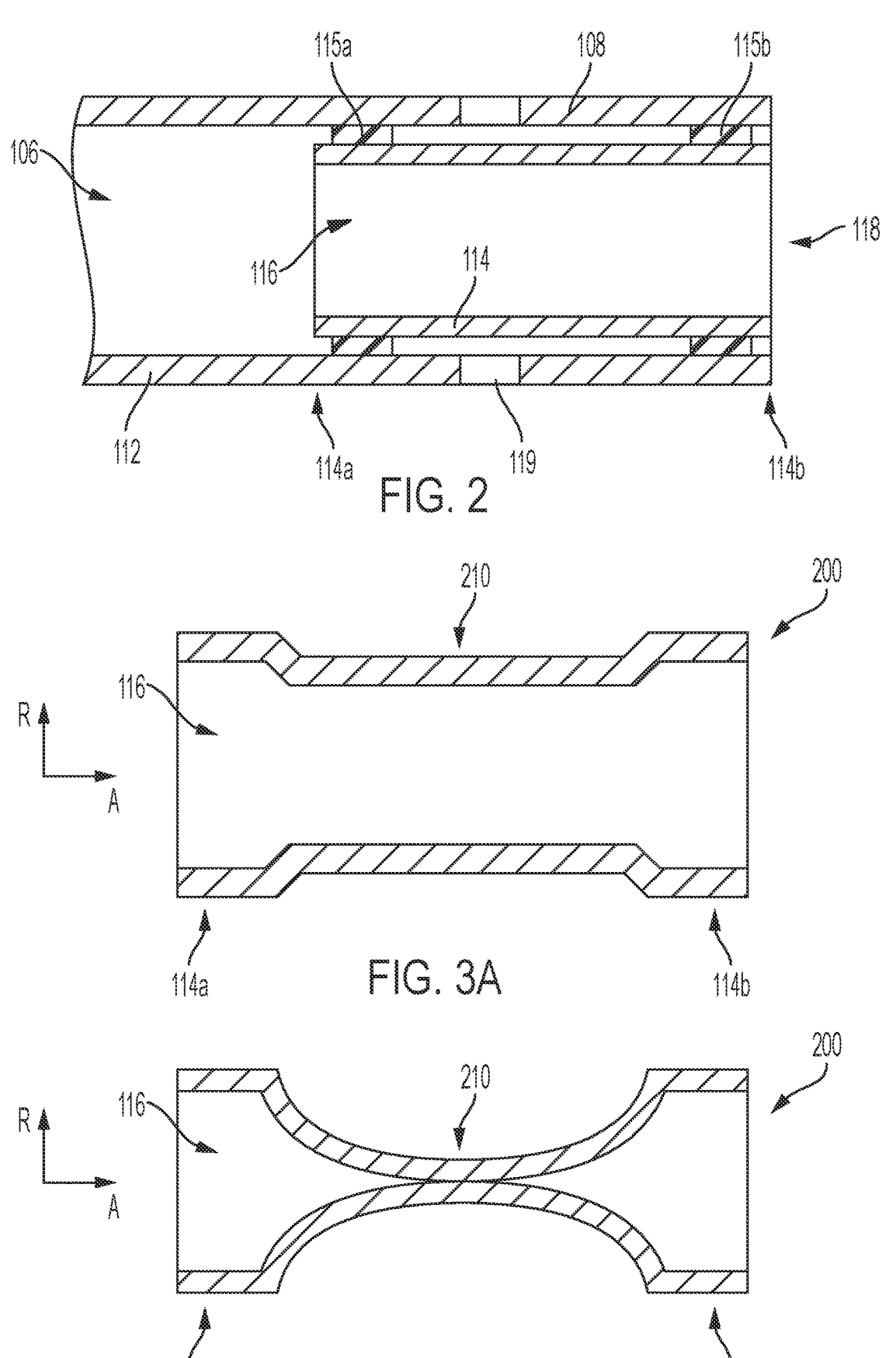
FIG. 2 schematically depicts a longitudinal cross-sectional view of the diaphragm of the thrombectomy device of FIG. 1A, according to one or more embodiments shown and described herein.
FIG. 3A schematically depicts a longitudinal cross-sectional view of a diaphragm for use in a thrombectomy device, according to one or more embodiments shown and described herein.
FIG. 3B schematically depicts a longitudinal cross-sectional view of the diaphragm of FIG. 3A, according to one or more embodiments shown and described herein.

Referring now to FIG. 2, the diaphragm 114 may extend between a proximal end 114a and a distal end 114b. In embodiments, the diaphragm 114 may be coupled (e.g., circumferentially coupled) to a first ring 115a at or near the proximal end 114a and may be coupled (e.g., circumferentially coupled) to a second ring 115b at or near the distal end 114b. The first ring 115a and the second ring 115b may be made from a stiffer material than the diaphragm 114, such as metal, plastic, Pebax, and the like. The stiffer material of the first ring 115a and the second ring 115b may prevent the first ring 115a and the second ring 115b from deforming when the diaphragm 114 moves between the open diaphragm configuration and the closed diaphragm configuration. The first ring 115a and the second ring 115b may be coupled (e.g., circumferentially coupled) to the outer body 112 within the lumen 106 by weld, adhesive, braze, or any other appropriate coupling. Accordingly, when the diaphragm 114 moves from the open diaphragm configuration to the closed diaphragm configuration, as depicted in FIGS. 1A and 1B, respectively, the proximal end 114a and the distal end 114b may remain coupled to the outer body 112 within the lumen 106, such that the diaphragm 114 provides an hourglass like shape when in the closed configuration.

Referring back to FIGS. 1A and 1B, in some embodiments, the diaphragm 114 may be coupled (e.g., circumferentially) to the outer body 112 without the first ring 115a and/or the second ring 115b. For example, in embodiments, the diaphragm 114 may be coupled to the outer body 112 at the proximal end 114a and the distal end 114b via adhesive or any other appropriate coupling. In some embodiments, the proximal end 114a and the distal end 114b may be differently coupled. For example, the diaphragm 114 may be coupled to the outer body 112 at the proximal end 114a via the first ring 115a and may be coupled to the catheter 110 at the distal end 114b via adhesive. In some embodiments, a ring coupling may provide increased rigidity, enabling the catheter to better hold its shape, while an adhesive coupling may provide increased flexibility to support movement of the diaphragm.

The diaphragm 114 may be made from any appropriately flexible material such as latex, silicon rubber, composite material, and the like. The diaphragm 114 may be sized and configured to move from the open diaphragm configuration to the closed diaphragm configuration when acted upon by sufficient vacuum pressure as provided by the vacuum 140. In particular, in some embodiments, the diaphragm 114 may be sized and configured (e.g., by selecting the length, thickness, and stiffness of the material) to move from the open diaphragm configuration to the closed diaphragm configuration when acted upon by the vacuum pressure of the vacuum 140 after a predetermined amount of time. For example, when acted upon by the vacuum pressure of the vacuum 140, the diaphragm 114 may move from the open diaphragm configuration to the closed diaphragm configuration after 1 second, after 2 seconds, etc.

Referring again to FIG. 2, in some embodiments, the outer body 112, the distal tip 108, or both may have one or more apertures 119 disposed adjacent the diaphragm 114 to facilitate moving the diaphragm 114 from the open diaphragm configuration to the closed diaphragm configuration. In particular, the one or more apertures 119 may create a pressure drop across the diaphragm 114 in the radial direction, which may promote movement of the diaphragm 114 in the radially-inward direction, e.g., from the open diaphragm configuration to the closed diaphragm configuration, under vacuum pressure. In such embodiments, the one or more apertures may have a circular shape, slit shape, or the like. As will be described in greater detail herein, the diaphragm 114 may be configured to return to the open diaphragm configuration from the closed diaphragm configuration upon removal or decrease of the vacuum pressure.

Referring back to FIGS. 1A and 1B, the lumen 106 of the catheter 110 may be in communication with the vacuum 140. The vacuum 140 may be configured to exert a continuous vacuum pressure through the thrombectomy device 100. Accordingly, the vacuum 140 may impart a vacuum pressure on the catheter 110 and the diaphragm 114. Disposed between the catheter 110 and the vacuum 140, the thrombectomy device 100 may include a container 130 for material collection. The container 130 may be in communication with both the catheter 110 and the vacuum 140 such that the vacuum 140 may impart the vacuum pressure on the catheter 110 through the container 130. In other words, the vacuum 140 may impart a pressure force acting in the direction of the directional arrows A, B, C, and D as depicted in FIG. 1A. Vacuum pressures may range for example, between about 0 mmHg to about-737 mmHg. Though various ranges are contemplated and possible.

The vacuum 140 may be fluidically coupled to the container 130 via one or more tubes 142. In some embodiments, the vacuum 140, the container 132, and/or the one or more tubes 142 fluidically coupling the vacuum 140 to the container 130. The container 130 may be fluidically coupled to the catheter 110 via one or more tubes 132. In particular, in some embodiments, the one or more tubes 132 may be coupled to the catheter 110 via a manifold 136. The manifold 136 may be positioned proximal the catheter 110.

The container 130 may be sized, oriented, and positioned to prevent the material 150 from exiting the container 130 (e.g., via the one or more tubes 132 or the one or more tubes 142). In some embodiments, this may be accomplished by coupling the one or more tubes 132 and the one or more tubes 142 to a top portion of the container 130 such that they are separated from a stored amount of the material 150, which may be disposed within a bottom portion of the container 130. Accordingly, when acted upon by the vacuum pressure from the vacuum 140, and when the diaphragm 114 is in the open diaphragm configuration, the material 150 may move through the thrombectomy device 100 and may be retained within the container 130. For example, when acted upon by the vacuum pressure from the vacuum 140 and when the diaphragm 114 is in the open diaphragm configuration, the material 150 may enter the distal tip 108 as indicated by the directional arrow A. The material 150 may then move through the lumen 106 of the catheter 110 as indicated by the directional arrow B. The material 150 may then pass from the catheter 110 to the container 130 via the one or more tubes 132 as indicated by the directional arrow C. The material 150 may then be retained within the container 130. In some embodiments, the container 130 may additionally or alternatively include a diaphragm check valve, one-way valve, filter, or other backflow prevention feature, which may prevent flow of the material 150 into the vacuum 140, such as described hereinabove.

Still referring to FIGS. 1A and 1B, the thrombectomy device 100 may include a fluid reservoir assembly 120 in communication with the lumen 106 of the catheter 110 and with the vacuum 140. In particular, the fluid reservoir assembly 120 may be fluidically coupled to the catheter 110 via one or more tubes 122. For example, the one or more tubes 122 may be coupled to the catheter 110 via the manifold 136. The fluid reservoir assembly 120 may include a fluid reservoir 124, which may house a fluid 128. In embodiments, the fluid 128 may be water, a saline solution, or other fluid. The fluid reservoir assembly 120 may include a valve 126 operably coupled to the fluid reservoir 124. For example, the valve 126 may be directly coupled to the fluid reservoir 124 or may be operably coupled to the fluid reservoir 124 along the one or more tubes 122, such as depicted.

The valve 126 may be moveable between an open valve configuration, such as depicted in FIG. 1B, and a closed valve configuration, such as depicted in FIG. 1A. When in the open valve configuration, the valve 126 may allow the fluid 128 to flow from the fluid reservoir 124 through the valve 126. When in the closed valve configuration, the valve 126 may prevent the fluid 128 from flowing through the valve 126. The valve 126 may be biased to the closed valve configuration and may be configured to move from the closed valve configuration to the open valve configuration when acted upon by a sufficient vacuum pressure. For example, in some embodiments, the valve 126 may be configured to move to the open valve configuration when acted upon by the full vacuum pressure of the vacuum 140 (e.g., when the diaphragm 114 is in the closed diaphragm configuration). The valve 126 may be configured to return to the closed valve configuration when acted upon by a vacuum pressure less than the full vacuum pressure of the vacuum 140 (e.g., when the diaphragm 114 is in the open diaphragm configuration). In embodiments, the valve 126 may be to the open position in response to pressure ranges from about −381 mmHg to about −737 mmHg and then reopens when vacuum pressure is between about 0 mmHg to about −381 mmHg.

In light of FIGS. 1A and 1B, it will now be appreciated that, in embodiments, the thrombectomy device 100 may be operable to provide intermittent (or cyclical) aspiration at the distal tip 108 of the catheter 110 in order to more efficiently remove a material 150 from a subject. As shown in FIG. 1A, in an initial state, the valve 126 may be in the closed valve configuration, and the diaphragm 114 may be in the open diaphragm configuration. The vacuum 140 may exert a continuous vacuum pressure such as described above. Accordingly, because the vacuum 140 is in communication with the catheter 110, and because the diaphragm 114 is in the open diaphragm configuration, the vacuum 140 may provide vacuum pressure at the distal tip 108 of the catheter 110. In this way, the thrombectomy device 100 may aspirate the material 150. The material 150 may therefore be removed from the subject and may enter the thrombectomy device 100 through the distal tip 108. The material 150 may then pass through the catheter 110 and into the container 130 in the direction of the directional arrows B and C. The material 150 may then be retained within the container 130.

After a predetermined amount of time, such as described hereinabove, the diaphragm 114 may move from the open diaphragm configuration to the closed diaphragm configuration as a result of the continuous vacuum pressure from the vacuum 140. For example, the timing of movement of the diaphragm may be a function of the pressure/vacuum application time and magnitude and the diaphragm material/ geometry. As vacuum is applied a more flexible diaphragm may take longer to close that a stiffer diaphragm. Accordingly, the diaphragm may be chosen based on the particular application. Once vacuum is reduced or removed the diaphragm 114 opens. Accordingly, the aspiration of the thrombectomy device 100 may be interrupted, and the thrombectomy device 100 may cease to aspirate the material 150 with the diaphragm 114 in the closed diaphragm configuration. As shown in FIG. 1B, the diaphragm 114 is in the closed diaphragm configuration, and further material 150 is blocked from entering the catheter 110 by the diaphragm 114.

When the diaphragm 114 moves to the closed diaphragm configuration, the vacuum 140 may continue to exert the continuous vacuum pressure. Accordingly, because the diaphragm is in the closed diaphragm configuration, the vacuum pressure acting on the valve 126 may increase. As a result, the valve 126 may move from the closed valve configuration to the open valve configuration. As shown in FIG. 1B, the diaphragm 114 is in the closed diaphragm configuration, and the valve 126 is in the open valve configuration. Accordingly, the vacuum 140 may exert a vacuum pressure on the fluid 128 through the valve 126. This may aspirate the fluid 128, which may therefore flow from the fluid reservoir 124 and into the container 130 in the direction of the directional arrows E and C. The fluid reservoir 124 may be open to atmospheric pressure. Accordingly, when the valve 126 is open, the vacuum pressure in catheter 112 drops sufficiently to allow the diaphragm 114 to move to the open configuration at least until the valve 126 again closes. It is noted that in embodiments tubing 122 may have a larger diameter than tubing 132 and/or 142, which may assist in tuning pressure drops/activations of the valve 126 and/or diaphragm.

The reduction in pressure acting on the diaphragm 114 may cause the diaphragm 114 to return to the open diaphragm configuration from the closed diaphragm configuration, such as depicted in FIG. 1A. Accordingly, when the diaphragm 114 returns to the open diaphragm configuration, the thrombectomy device 100 may resume aspirating the material 150. Opening of the diaphragm 114 may in turn cause a decrease in pressure acting on the valve 126, and the valve 126, which may be biased to the closed valve configuration, may return to the closed valve configuration from the open valve configuration, such as depicted in FIG. 1A. The thrombectomy device 100 may therefore continue to cycle moving the diaphragm 114 and the valve 126 from open to closed configurations in this manner.

In particular, in embodiments, the diaphragm 114 may move from the open diaphragm configuration to the closed diaphragm configuration after a first predetermined time and may move from the closed diaphragm configuration to the open diaphragm configuration after a second predetermined time. For example, the diaphragm 114 may be moved between the open and closed diaphragm configurations at a frequency of about 0.5 to about 2 HZ, though other ranges are contemplated and possible. Accordingly, the diaphragm 114 may continuously cycle between the open diaphragm configuration and the closed diaphragm configuration. More specifically, a method of use of the thrombectomy device 100 may include continuously cycling the diaphragm 114 between the open diaphragm configuration and the closed diaphragm configuration at a predetermined time interval, such as described.

Still referring to FIGS. 1A and 1B, as the thrombectomy device 100 continues to cycle, such as described, the thrombectomy device 100 may accordingly provide intermittent or interrupted aspiration at the distal tip 108 of the catheter 110. In other words, while the vacuum 140 exerts a continuous vacuum pressure, the thrombectomy device 100 may exert a vacuum pressure on the material 150 intermittently. This may be beneficial in some applications as intermittent aspiration of the material 150 may prevent blockage or clogging of the thrombectomy device 100. For example, the intermittent aspiration of the material 150 combined with the cycling of the diaphragm 114 between the open diaphragm position and the closed diaphragm position may allow the diaphragm 114 to macerate the material 150, which may break apart larger portions of the material 150. This may optionally allow the thrombectomy device 100 to remove the material 150 piece-by-piece, rather than attempting to remove it all in one go. Additionally, the intermittent aspiration of the fluid 128 may cyclically flush the one or more tubes 122 and the one or more tubes 132, which may help in remove blockage or clogs within thrombectomy device 100.

Figure 8:
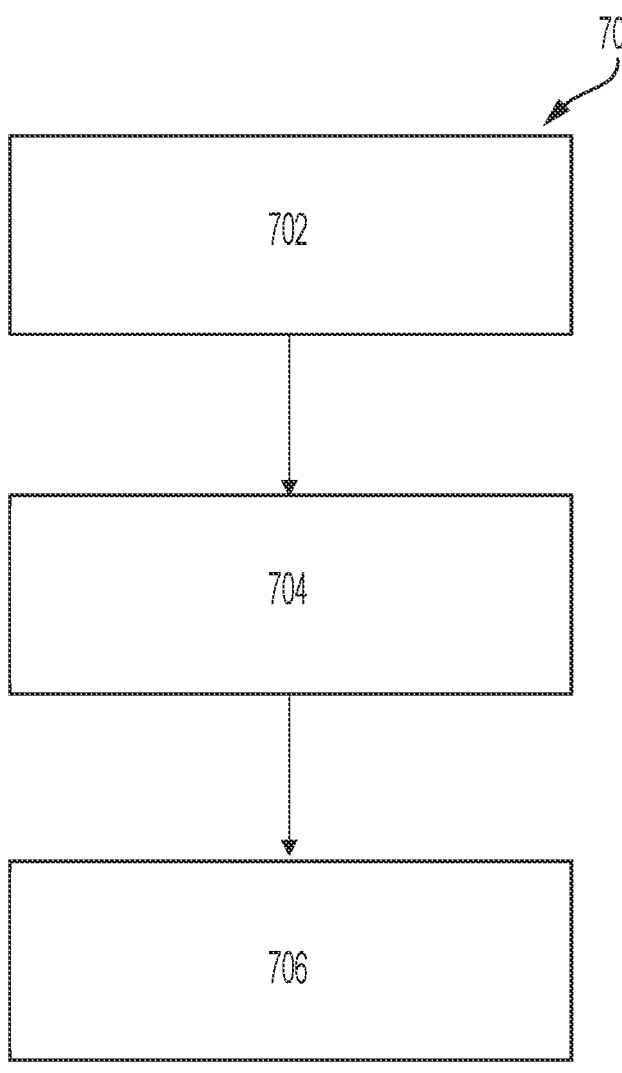
FIG. 8 schematically depicts a flowchart illustrating a method of performing a thrombectomy procedure, according to one or more embodiments shown and described herein.

Referring now to FIG. 8, in light of FIGS. 1A and 1B, it will now be appreciated that a method 700 of performing a thrombectomy may include a first step 702 of inserting the thrombectomy device 100 into a subject. The method 700 may then include a second step 704 of activating the vacuum 140 such that a continuous vacuum pressure is exerted on the diaphragm 114. As described with reference to FIGS. 1A and 1B, the continuous vacuum pressure may cause a cycling of the diaphragm 114 between the open diaphragm configuration and the closed diaphragm configuration. In particular, this cycling may occur at a predetermined time interval. The method 700 may then include a third step 706 of removing the material 150 from the subject with the thrombectomy device 100. As described with reference to FIGS. 1A and 1B, the removing of the material 150 from the subject may include macerating the material 150 with the diaphragm 114 as the diaphragm 114 cycles between the open diaphragm position and the closed diaphragm position.

Referring now to FIGS. 3A and 3B, an embodiment of a diaphragm 200 is schematically depicted which may form part of a thrombectomy device as described above. The diaphragm 200 may be substantially similar to the above-described diaphragm 114. Accordingly, like numbers are used to refer to like features. For example, the diaphragm may have a proximal end 114a and a distal end 114b. Additionally, the diaphragm 200 may be moveable between an open diaphragm configuration and a closed diaphragm configuration such as described above. Accordingly, the diaphragm 200 may define a diaphragm passage 116 when in the open diaphragm configuration, such as depicted in FIG. 3A. The diaphragm passage 116 may be closed or substantially closed when in the closed diaphragm configuration, such as depicted in FIG. 3B.

Disposed between the proximal end 114a and a distal end 114b, the diaphragm 200 may define a collapsing portion 210, configured to collapse under sufficient vacuum pressure. The collapsing portion 210 of the diaphragm 200 may be positioned radially inward (e.g., in the radial direction R of the depicted coordinate system) relative to the proximal end 114a and the distal end 114b. That is, the collapsing portion 210 may provide a reduced diameter region relative to the proximal end 114a and the distal end 114b. This collapsing portion 210 of the diaphragm 200 may cause the diaphragm 200 to be predisposed toward the moving to the closed diaphragm configuration at the collapsing portion 210. This may be beneficial in some embodiments, as the diaphragm 200 may more easily move from the open diaphragm configuration to the closed diaphragm configuration.

Referring now to FIGS. 4A-4D, an embodiment of a catheter 110' which may form part of a thrombectomy device as described above is schematically depicted. The catheter 110' is substantially similar to the catheter 110 described hereinabove. Accordingly, like numbers are used to refer to like features. For example, the catheter 110' may have an outer body 112 that has a distal end 102 and a proximal end 104. The catheter 110' may include a diaphragm 300.

Figures 4A, 4B, 4C, 4D, 5, 6:
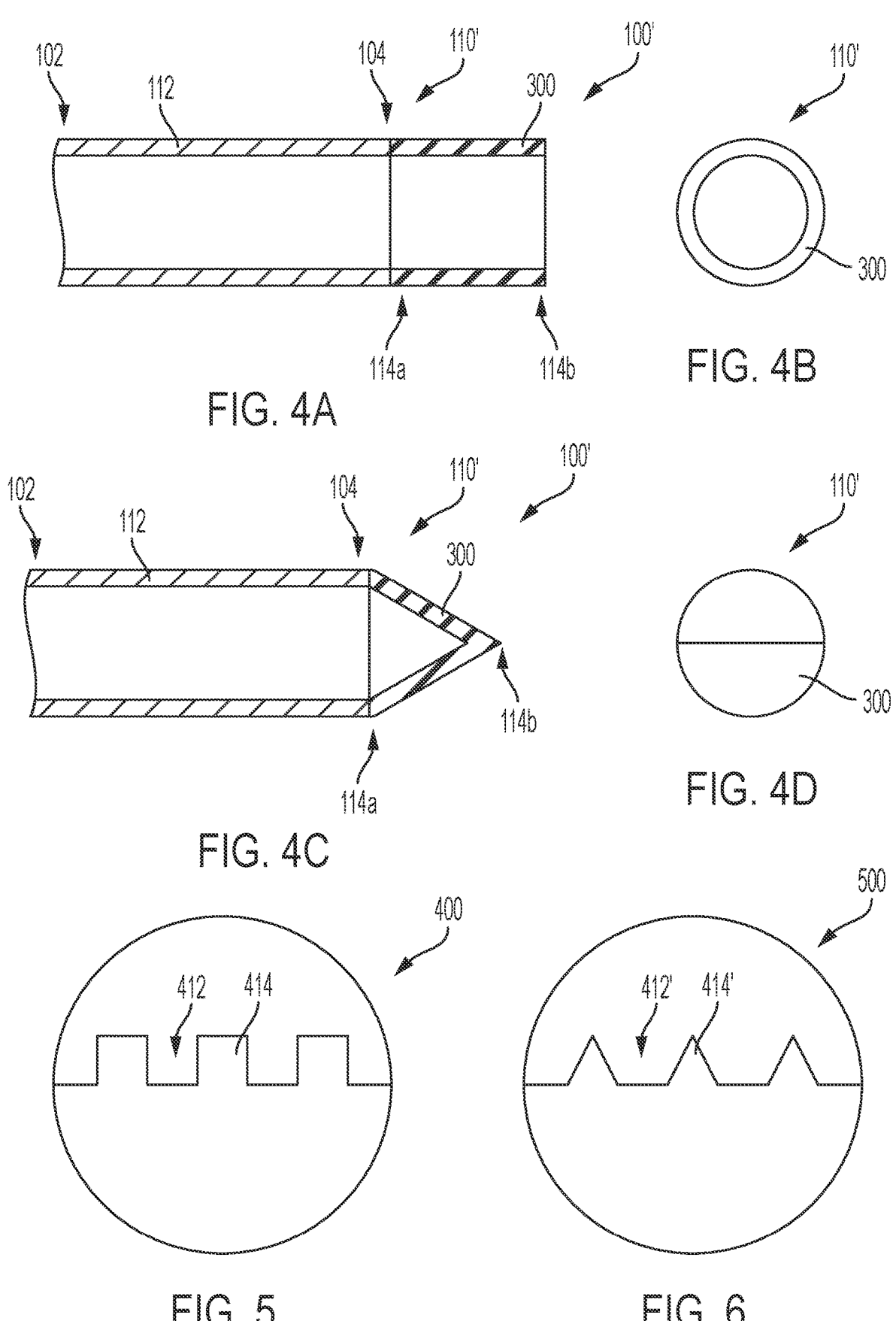
FIG. 4A schematically depicts a longitudinal cross-sectional view of a thrombectomy device having a catheter and a diaphragm in an open diaphragm configuration, according to one or more embodiments shown and described herein.
FIG. 4B schematically depicts an axial view of the catheter and diaphragm of FIG. 4A, according to one or more embodiments shown and described herein.
FIG. 4C schematically depicts a longitudinal cross-sectional view of the catheter and diaphragm in a closed diaphragm configuration of FIG. 4A, according to one or more embodiments shown and described herein.
FIG. 4D schematically depicts an axial view of the catheter and diaphragm of FIG. 4A, according to one or more embodiments shown and described herein.
FIG. 5 schematically depicts an axial view of a diaphragm of a thrombectomy device, according to one or more embodiments shown and described herein.
FIG. 6 schematically depicts an axial view of a diaphragm of a thrombectomy device, according to one or more embodiments shown and described herein.

The diaphragm 300 may be substantially similar to the above-described diaphragms 114 and 200. Accordingly, like numbers are used to refer to like features. For example, the diaphragm may have a proximal end 114a and a distal end 114b. Additionally, the diaphragm 300 may be moveable between an open diaphragm configuration and a closed diaphragm configuration such as described above. Accordingly, the diaphragm 300 may define a diaphragm passage 116 when in the open diaphragm configuration, such as depicted in FIGS. 4A and 4B. The diaphragm passage 116 may be closed or substantially closed when in the closed diaphragm configuration, such as depicted in FIGS. 4C and 4D. The catheter 110' may operate in a substantially similar manner as described above with respect to FIGS. 1A-1B.

Still referring to FIGS. 4A-4D, the diaphragm 300 may be coupled to the outer body 112 of the catheter 110'. In particular, the proximal end 114a of the diaphragm 300 may be coupled to and extend from the distal end 102 of the outer body 112, as opposed to being positioned within the outer body 112 or within a distal tip, such as the distal tip 108 depicted in FIG. 1A. Accordingly, the diaphragm 300 may function as a distal tip of the catheter 110', and the catheter 110' may not include a separate distal tip distinct from the diaphragm 300. The diaphragm 300 may be coupled to the outer body 112 via adhesive, interference fit, one or more attachment rings such as the first ring 115a or the second ring 115b described above with reference to FIG. 2, or any other appropriate coupling.

Still referring to FIGS. 4A-4D, the distal end 114b of the diaphragm 300 may be unconstrained by the outer body 112 of the catheter 110'. Accordingly, the distal end 114b, unlike the proximal end 114a, may close or substantially close when in the closed diaphragm configuration, such as depicted in FIGS. 4C and 4D, similar to a duck-bill valve. That is, the diaphragm 300 may flatten at the distal end 114b to close the diaphragm 300. Accordingly, under sufficient vacuum pressure as described above, the distal end 114b may move between the diaphragm closed configuration and the diaphragm open configuration, such as described above. Movement of the distal end 114b between the open and closed diaphragm configurations may optionally assist in macerating, or breaking apart, the material 150 disposed in the vessel.

Referring now to FIG. 5, an embodiment of a diaphragm 400 is schematically depicted. The diaphragm 400 may be substantially similar to the above-described diaphragms 114, 200, and 300. Accordingly, the diaphragm 400 may be moveable between an open diaphragm configuration and a closed diaphragm configuration such as described above.

The diaphragm 400 may include a plurality of protrusions, such as top protrusions 412 and bottom protrusions 414. In embodiments, the top protrusions 412 and the bottom protrusions 414 may extend (e.g., into and out of FIG. 5) to form ridges. In other embodiments, cither the top protrusions 412 or the bottom protrusions 414 or both may not extend a significant distance to form ridges and, instead, may extend a shorter distances (e.g., into and out of FIG. 5) to form bumps. In some embodiments, the top protrusions 412 and the bottom protrusions 414 may be arranged such the top protrusions 412 and the bottom protrusions 414 form and interlocking pattern when the diaphragm 400 is in the closed diaphragm configuration, such as depicted. As will now be appreciated in light of FIG. 5, in some embodiments, the top protrusions 412 and the bottom protrusions 414 may assist in macerating, or breaking apart, the material 150 disposed therein. In some embodiments, this may reduce the size of clumps or clots disposed within the material 150 and may thereby reduce the likelihood that the material 150 clogs or otherwise obstructs the catheter 110'. The protrusions as provided herein, may be incorporated into any of the diaphragms as described herein. For example, the protrusions may be provided at the distal end 114b' of the diaphragm 300, or between the proximal end 114a and the distal end 114b in diaphragms 114 and 200. That is the protrusions may be formed at a location wherein an axial cross-section of the diaphragm closes when moved to the closed diaphragm configuration.

Still referring to FIG. 5, as depicted, the top protrusions 412 and the bottom protrusions 414 may have a substantially rectangular or tooth-like geometry. However, other geometries are contemplated and possible. For example, referring now to FIG. 6, a diaphragm 500 may have top protrusions 412' and bottom protrusions 414' that each have a triangular or tapered geometry. In other embodiments, the top protrusions 412' and the bottom protrusions 414' may have a rounded geometry or any other raised geometry.

Figure 7A:
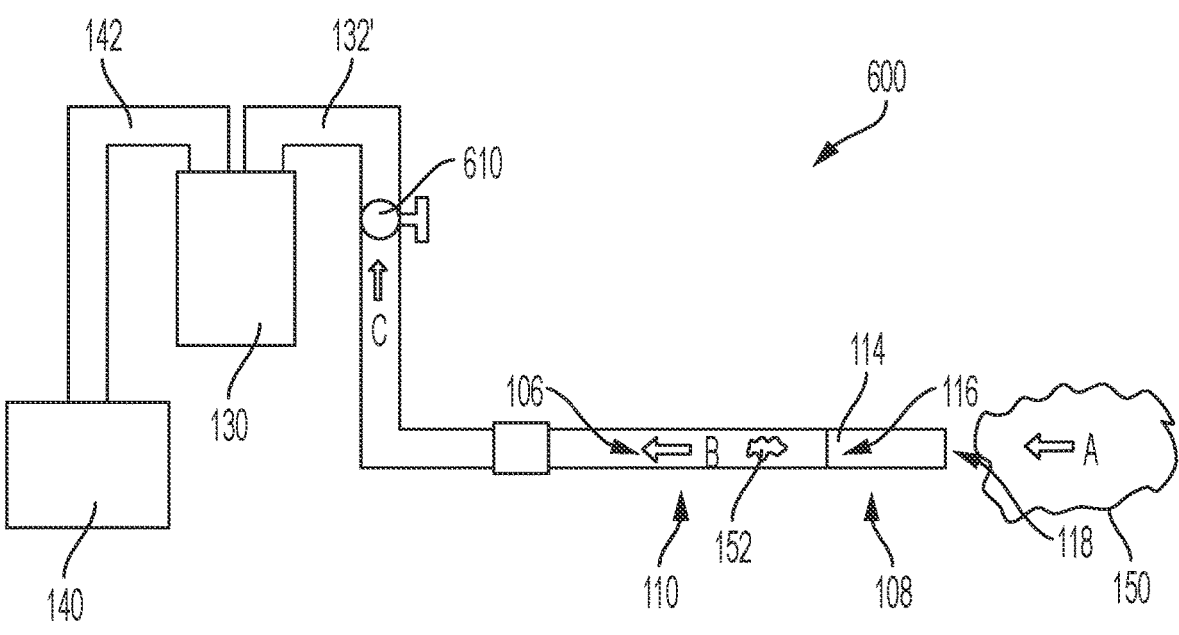
FIG. 7A schematically depicts a diagram of a thrombectomy device having a diaphragm in an open diaphragm configuration and a valve in an valve open configuration, according to one or more embodiments shown and described herein.
Figure 7B:
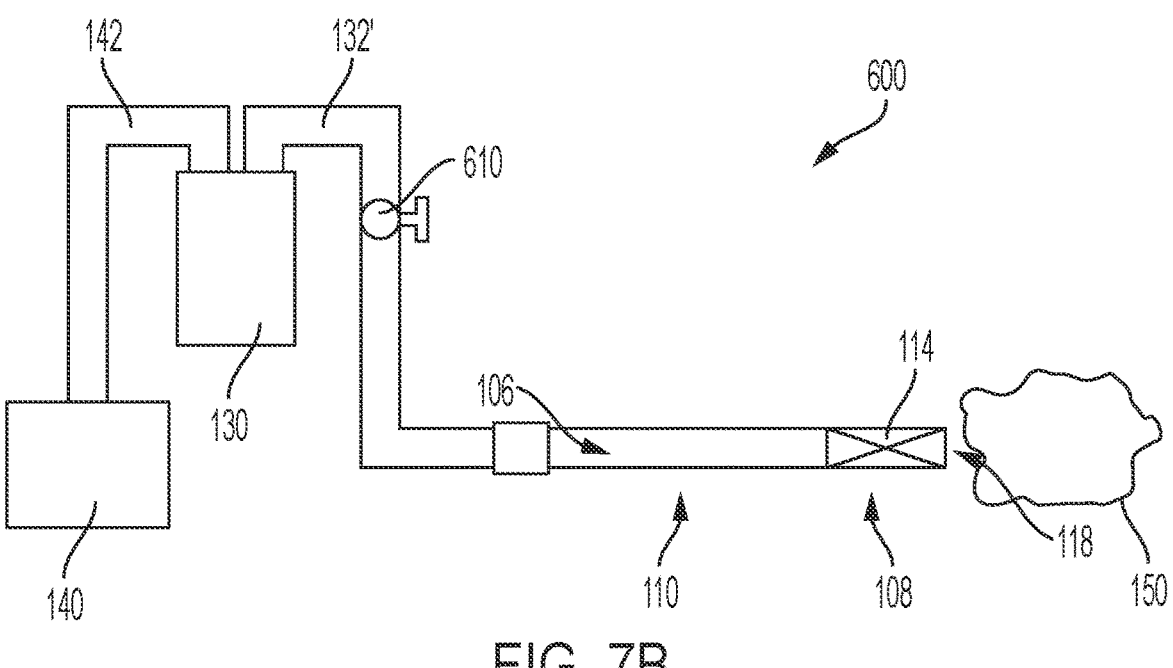
FIG. 7B schematically depicts of the diaphragm of FIG. 7A in a closed diaphragm configuration and the valve in the open valve configuration, according to one or more embodiments shown and described herein.
Figure 7C:
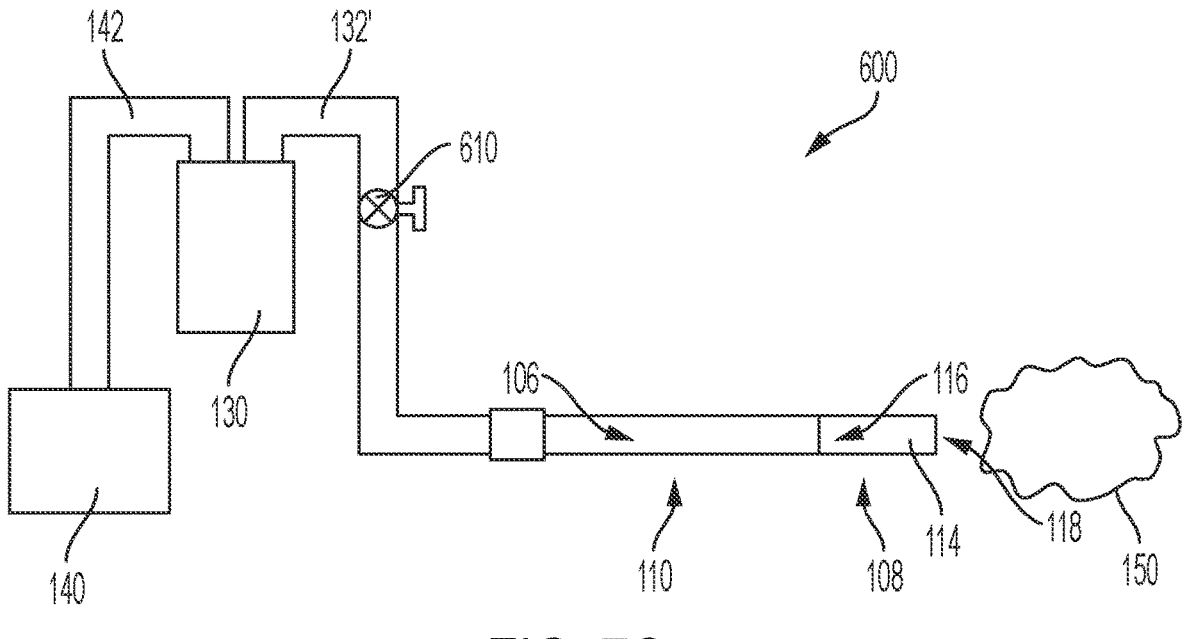
FIG. 7C schematically depicts of the diaphragm in the open diaphragm configuration and the valve in a closed valve configuration.

Referring now to FIGS. 7A-C, an embodiment of a thrombectomy device 600 is schematically depicted. The thrombectomy device 600 is substantially similar to the thrombectomy device 100. Accordingly, like numbers are used to refer to like features. For example, the thrombectomy device 600 may have a catheter 110 for aspirating a material 150. The catheter 110 may include a diaphragm 114 and may be fluidically coupled to a container 130 and to a vacuum 140 such as described hereinabove. In particular, in some embodiments, the catheter 110 may be fluidically coupled to the container 130 via one or more tubes 132, and the container 130 may be fluidically coupled to the vacuum 140 via one or more tubes 142. Accordingly, the material 150 may travel through the thrombectomy device 600 in a direction such as depicted by the directional arrows A and C.

The thrombectomy device 600 may include a valve 610 that is movable between an open valve configuration and a closed valve configuration. The valve 610 may be open in the open valve configuration and may be closed or substantially closed in the closed valve configuration. The valve 610 may be configured to cycle between the open valve configuration and the closed valve configuration. For example, in some embodiments, the valve 610 may be configured to cycle between the open valve configuration and the closed valve configuration at a fixed frequency. In other embodiments, the valve 610 may be biased to the open valve configuration and may be configured to move from the open valve configuration to the closed valve configuration when a vacuum pressure acting on the valve 610 exceeds a predetermined threshold. In some such embodiments, the valve 610 may be configured to return to the open valve configuration after a predetermined amount of time. In some embodiments, an actuator and/or a timing device may be used to operate the valve 610 at a desired frequency. In some embodiments, feedback such as from pressure sensors incorporated into the system may provide feedback such that opening and closing of the valve occurs in response to a detected pressure such as at the valve 610, at the diaphragm, or the like.

As depicted in FIGS. 7A-C, in embodiments, the valve 610 may be disposed between the container 130 and the catheter 110. Specifically, in some embodiments, the valve 610 may be disposed along the one or more tubes 132'. Accordingly, when in the open valve configuration, the valve 610 may allow the diaphragm 114 and the distal tip 108 to experience the continuous vacuum pressure from the vacuum 150. Additionally, when in the open valve configuration, the valve 610 may allow the material 150 to flow through the valve 610. Conversely, when in the closed valve configuration, the valve 610 may prevent the diaphragm 114 and the distal tip 108 from experiencing the continuous vacuum pressure from the vacuum 150. Additionally, when in the closed valve configuration, the valve 610 may prevent the material 150 from flowing through the valve 610.

Accordingly, in light of the FIGS. 7A-7C, it will be appreciated that the thrombectomy device 600 may aspirate the material 150 when the valve 610 and the diaphragm 114 are both open (i.e. the valve 610 is in the open valve configuration and the diaphragm 114 is in the open diaphragm configuration). Conversely, the thrombectomy device 600 may cease to aspirate the material 150 when the valve 610 or the diaphragm 114 or both are closed (e.g., when the valve is in the closed valve configuration or when the diaphragm 114 is in the closed diaphragm configuration).

Referring to FIG. 7A, the valve 610 of the thrombectomy device 600 is depicted in the open valve configuration, and the diaphragm 114 of the catheter 110 is depicted in the open diaphragm configuration. Accordingly, as depicted, the vacuum 140 may exert a continuous vacuum pressure, and the material 150 may be aspirated by the thrombectomy device 600.

As described hereinabove, the diaphragm 114 may move from the open diaphragm configuration to the closed diaphragm configuration when acted upon by the continuous vacuum pressure of the vacuum 140 after a predetermined amount of time. For example, a controller and/an actuator (e.g., a solenoid valve) may be used and operated to open/ close after a predetermined time. When the diaphragm 114 moves from the open diaphragm configuration to the closed diaphragm configuration, the valve 610 may remain, at least temporarily, in the open valve configuration. For example, as depicted in FIG. 7B, the valve 610 is depicted in the open valve configuration, and the diaphragm 114 is depicted in the closed diaphragm configuration.

Referring to FIG. 7B, in this instance, because the diaphragm 114 is in the closed diaphragm configuration, the thrombectomy device 600 may cease to aspirate the material 150. At the same time, because the diaphragm 114 is in the closed diaphragm configuration and is held in the closed diaphragm configuration by the vacuum pressure, the vacuum pressure may build within the thrombectomy device 600 between the vacuum 140 and the diaphragm 114. As a result, the valve 610 may be subjected to a greater vacuum pressure. This increase in vacuum pressure experienced by the valve 610 may exceed the predetermined threshold required to move the valve 610 from the open valve configuration to the closed valve configuration. Such as threshold may include any threshold pressure such as, but not limited to, −381 mmHg to about −737 mmHg. Accordingly, under sufficient vacuum pressure, the valve 610 may move from the open valve configuration to the closed valve configuration. As will now be appreciated, in embodiments, the valve 610 may be configured to move from the open valve configuration to the closed valve configuration a predetermined amount of time after the diaphragm 114 moved from the open diaphragm configuration to the closed diaphragm configuration, such as between about 0.5 seconds and about 2 seconds, though other timeframes are contemplated and possible. When the valve 610 moves from the open valve configuration to the closed valve configuration, the diaphragm 114 may be relieved of the continuous vacuum pressure from the vacuum 140. Accordingly, the diaphragm 114 may return to the open diaphragm configuration from the closed diaphragm configuration. For example, as depicted in FIG. 7C, the diaphragm 114 is in the open diaphragm configuration, and the valve 610 is in the closed valve configuration.

Still referring to FIG. 7B, in some embodiments, the valve 610 may be configured or controlled to move from the open valve configuration to the closed valve configuration after a predetermined amount of time, after the diaphragm 114 moves from the closed diaphragm configuration to the open diaphragm configuration. Such as within about 5 seconds, such as within about 3 seconds, such as within about 2 seconds, or the like. The predetermined time may therefore be considered to be a delay between the opening of the diaphragm 114 and the opening of the valve 610. This delay may optionally allow the thrombectomy device to ensure complete reopening of the diaphragm thereby improving initial onset aspiration after the valve 610 moves to the open valve configuration. Accordingly, in one example, if the diaphragm 114 is configured to move from the open diaphragm configuration to the closed diaphragm configuration after about 2 seconds of experiencing the continuous vacuum pressure of the vacuum 140, then the valve 610 may be configured to move from the open valve configuration to the closed valve configuration after about 3 second. Accordingly, after about 3 seconds, the diaphragm 114 may be transition back to the open diaphragm configuration, and the valve 610 may be in the closed valve configuration, such as depicted in FIG. 7C. Additional timeframes are contemplated and possible.

Referring now to FIG. 7C, the diaphragm 114 is depicted in the open diaphragm configuration, and the valve 610 is depicted in the closed valve configuration. The valve 610, in some embodiments, may be configured such that the valve 610 moves from the closed valve configuration to the open valve configuration after a predetermined amount of time. For example, in some such embodiments, the valve 610 may move from the closed valve configuration to the open valve configuration after about 1 second, about 2 seconds, etc.

In embodiments, the movement of the valve 610 may be controlled by a control system (not depicted). For example, the valve 610 may be motorized or otherwise actuatable via an actuator, which may be controlled via a controller (e.g., a computer). Accordingly, in embodiments, the valve 610 may be moved to the open valve configuration while the diaphragm 114 is in the open diaphragm configuration. For example, as shown in FIG. 7A, the valve 610 is in the open valve configuration and the diaphragm 114 is in the open diaphragm configuration. Accordingly, the thrombectomy device 600 may resume aspiration of the material 150.

In light of FIGS. 7A-7C, it will now be appreciated that the valve 610 may cycle between the open valve configuration and the closed valve configuration, and the diaphragm 114 may cycle between the open diaphragm configuration and the closed diaphragm configuration, such as described. Accordingly, the thrombectomy device 600 may provide interrupted aspiration of the material 150.

Embodiments can be further described with reference to the following numerical clauses:

1. A thrombectomy device for removing a material from a subject, comprising: a catheter comprising an outer body defining a lumen extending therethrough; a diaphragm coupled to the catheter and moveable between an open diaphragm configuration and a closed diaphragm configuration, wherein the diaphragm allows movement of the material through the lumen when in the open diaphragm configuration and prevents movement of the material through the lumen when in the closed diaphragm configuration; and a vacuum in communication with the lumen and operable to exert a vacuum pressure on the diaphragm, wherein the vacuum pressure is operable to move the diaphragm from the open diaphragm configuration to the closed diaphragm configuration.

2. The thrombectomy device of clause 1, wherein the diaphragm comprises one or more protrusions.

3. The thrombectomy device of any preceding clause, wherein the catheter has a distal end and the diaphragm is coupled to the catheter at the distal end.

4. The thrombectomy device of any preceding clause, wherein the catheter has a distal end and the diaphragm is disposed within the lumen at the distal end.

5. The thrombectomy device of any preceding clause, wherein the diaphragm defines a proximal end, a distal end, and a collapsing portion, the collapsing portion having a reduced diameter relative to the proximal end and the distal end.

6. The thrombectomy device of any preceding clause, further comprising a fluid reservoir assembly in communication with the lumen and operable to exert a pressure on the diaphragm, wherein the pressure is operable to move the diaphragm from the closed diaphragm configuration to the open diaphragm configuration, and wherein the fluid reservoir assembly comprises a fluid reservoir and a valve operably coupled to the fluid reservoir, wherein the valve is movable between an open valve configuration and a closed valve configuration, wherein the valve allows a fluid to flow from the fluid reservoir and through the valve when in the open valve configuration and prevents the fluid from flowing through the valve when in the closed valve configuration.

7. The thrombectomy device of any preceding clause, wherein the valve is configured to move from the closed valve configuration to the open valve configuration when the diaphragm is in the closed diaphragm configuration.

8. The thrombectomy device of any preceding clause, wherein the fluid reservoir assembly exerts the pressure on the diaphragm when the valve is in the open valve configuration.

9. The thrombectomy device of any preceding clause, wherein the vacuum is configured to exert a continuous vacuum pressure.

10. The thrombectomy device of any preceding clause, wherein the vacuum pressure is operable to move the diaphragm from the open diaphragm configuration to the closed diaphragm configuration after a predetermined amount of time.

11. A thrombectomy device for removing a material from a subject, comprising: a catheter comprising an outer body defining a lumen extending therethrough; a diaphragm disposed within the lumen and moveable between an open diaphragm configuration and a closed diaphragm configuration, wherein the diaphragm allows movement of the material through the lumen when in the open diaphragm configuration and prevents movement of the material through the lumen when in the closed diaphragm configuration; a vacuum in communication with the lumen and operable to exert a vacuum pressure on the diaphragm, wherein the vacuum pressure is operable to move the diaphragm from the open diaphragm configuration to the closed diaphragm configuration; and a fluid reservoir assembly in communication with the lumen and operable to exert a pressure within the thrombectomy device, wherein the pressure exerted by the fluid reservoir assembly is operable to move the diaphragm from the closed diaphragm configuration to the open diaphragm configuration.

12. The thrombectomy device of any of clauses 1-11, wherein the vacuum and the fluid reservoir assembly are operable to continuously cycle the diaphragm between the open diaphragm configuration and the closed diaphragm configuration.

13. The thrombectomy device of any of clauses 1-12, wherein the catheter has a distal end and the diaphragm is disposed within the lumen at the distal end.

14. The thrombectomy device of any of clauses 1-13, wherein the diaphragm moves from the open diaphragm configuration to the closed diaphragm configuration after a first predetermined time and moves from the closed diaphragm configuration to the open diaphragm configuration after a second predetermined time.

15. A method of performing a thrombectomy comprising: inserting a thrombectomy device into a subject, the thrombectomy device comprising: a catheter comprising an outer body defining a lumen extending therethrough; a diaphragm disposed within the lumen and moveable between an open diaphragm configuration and a closed diaphragm configuration, wherein the diaphragm allows movement of material through the lumen when in the open diaphragm configuration and prevents movement of the material through the lumen when in the closed diaphragm configuration; and a vacuum in communication with the lumen and operable to exert a vacuum pressure on the diaphragm, wherein the vacuum pressure is operable to move the diaphragm from the open diaphragm configuration to the closed diaphragm configuration; and removing the material from the subject with the thrombectomy device.

16. The method of any preceding clause, wherein the thrombectomy device further comprises a fluid reservoir assembly in communication with the lumen and operable to exert a pressure on the diaphragm, wherein the pressure is operable to move the diaphragm from the closed diaphragm configuration to the open diaphragm configuration.

17. The method of any preceding clause further comprising activating the vacuum such that a continuous vacuum pressure is exerted on the diaphragm.

18. The method of any preceding clause, further comprising cycling the diaphragm between the open diaphragm configuration and the closed diaphragm configuration.

19. The method of any preceding clause, further comprising cycling the diaphragm between the open diaphragm configuration and the closed diaphragm configuration at a predetermined time interval.

20. The method of any preceding clause, further comprising macerating the material from the subject with the diaphragm.

21. A method of removing material from a vessel using the thrombectomy device of any of clauses 1-15, the method comprising: inserting the thrombectomy to a target location; activating a vacuum in communication with the thrombectomy device.

22. The method of clause 21, further cyclically opening and closing a diaphragm to the thrombectomy device to macerate material received from within the vessel.

It should now be understood that embodiments of the present disclosure are directed to a thrombectomy device for removing a material, such as occlusive material, from a subject. The thrombectomy device may generally include a catheter, a diaphragm, and a vacuum. The catheter may include an outer body defining a lumen extending therethrough. The diaphragm may be coupled to the catheter and moveable between an open diaphragm configuration and a closed diaphragm configuration. The diaphragm may allow movement of the material through the lumen when in the open diaphragm configuration and prevents movement of the material through the lumen when in the closed diaphragm configuration. The vacuum may be in communication with the lumen and may be operable to exert a vacuum pressure on the diaphragm. The vacuum pressure may be operable to move the diaphragm from the open diaphragm configuration to the closed diaphragm configuration. Accordingly, the diaphragm may cycle between the open diaphragm configuration and the closed diaphragm configuration. This may allow the thrombectomy device to aspirate the material intermittently, which may prevent blockage or clogging of the thrombectomy device. This may enable the thrombectomy device to remove material and, more specifically, occlusions from the subject more effectively.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

The invention claimed is:

1. A thrombectomy device for removing a material from a subject, comprising:
   a catheter comprising an outer body defining a lumen extending therethrough;
   a diaphragm coupled to the catheter and moveable between an open diaphragm configuration and a closed diaphragm configuration, wherein the diaphragm allows movement of the material through the lumen when in the open diaphragm configuration and prevents movement of the material through the lumen when in the closed diaphragm configuration; and
   a vacuum generation device in communication with the lumen and operable to exert a vacuum pressure on the diaphragm, wherein the vacuum pressure, when exerted, is operable to move the diaphragm from the open diaphragm configuration to the closed diaphragm configuration.

2. The thrombectomy device of claim 1, wherein the diaphragm comprises one or more protrusions.

3. The thrombectomy device of claim 1, wherein the catheter has a distal end and the diaphragm is coupled to the catheter at the distal end.

4. The thrombectomy device of claim 1, wherein the catheter has a distal end and the diaphragm is disposed within the lumen at the distal end.

5. The thrombectomy device of claim 1, wherein the diaphragm defines a proximal end, a distal end, and a collapsing portion, the collapsing portion having a reduced diameter relative to the proximal end and the distal end.

6. The thrombectomy device of claim 1, further comprising a fluid reservoir assembly in communication with the lumen and operable to exert a pressure on the diaphragm, wherein the pressure is operable to move the diaphragm from the closed diaphragm configuration to the open diaphragm configuration, and wherein the fluid reservoir assembly comprises a fluid reservoir and a valve operably coupled to the fluid reservoir, wherein the valve is movable between an open valve configuration and a closed valve configuration, wherein the valve allows a fluid to flow from the fluid reservoir and through the valve when in the open valve configuration and prevents the fluid from flowing through the valve when in the closed valve configuration.

7. The thrombectomy device of claim 6, wherein the valve is configured to move from the closed valve configuration to the open valve configuration when the diaphragm is in the closed diaphragm configuration.

8. The thrombectomy device of claim 6, wherein the fluid reservoir assembly exerts the pressure on the diaphragm when the valve is in the open valve configuration.

9. The thrombectomy device of claim 1, wherein the vacuum generation device is configured to exert a continuous vacuum pressure.

10. The thrombectomy device of claim 1, wherein the vacuum pressure is operable to move the diaphragm from the open diaphragm configuration to the closed diaphragm configuration after a predetermined amount of time.

11. A thrombectomy device for removing a material from a subject, comprising:
a catheter comprising an outer body defining a lumen extending therethrough;
a diaphragm disposed within the lumen and moveable between an open diaphragm configuration and a closed diaphragm configuration, wherein the diaphragm allows movement of the material through the lumen when in the open diaphragm configuration and prevents movement of the material through the lumen when in the closed diaphragm configuration;
a vacuum generation device in communication with the lumen and operable to exert a vacuum pressure on the diaphragm, wherein the vacuum pressure, when exerted, is operable to move the diaphragm from the open diaphragm configuration to the closed diaphragm configuration; and
a fluid reservoir assembly in communication with the lumen and operable to exert a pressure within the thrombectomy device, wherein the pressure exerted by the fluid reservoir assembly is operable to move the diaphragm from the closed diaphragm configuration to the open diaphragm configuration.

12. The thrombectomy device of claim 11, wherein the vacuum generation device and the fluid reservoir assembly are operable to continuously cycle the diaphragm between the open diaphragm configuration and the closed diaphragm configuration.

13. The thrombectomy device of claim 11, wherein the catheter has a distal end and the diaphragm is disposed within the lumen at the distal end.

14. The thrombectomy device of claim 11, wherein the diaphragm moves from the open diaphragm configuration to the closed diaphragm configuration after a first predetermined time and moves from the closed diaphragm configuration to the open diaphragm configuration after a second predetermined time.

15. A method of performing a thrombectomy comprising:
inserting a thrombectomy device into a subject, the thrombectomy device comprising:
a catheter comprising an outer body defining a lumen extending therethrough;
a diaphragm disposed within the lumen and moveable between an open diaphragm configuration and a closed diaphragm configuration, wherein the diaphragm allows movement of material through the lumen when in the open diaphragm configuration and prevents movement of the material through the lumen when in the closed diaphragm configuration; and
a vacuum generation device in communication with the lumen and operable to exert a vacuum pressure on the diaphragm, wherein the vacuum pressure, when exerted, is operable to move the diaphragm from the open diaphragm configuration to the closed diaphragm configuration; and
removing the material from the subject with the thrombectomy device.

16. The method of claim 15, wherein the thrombectomy device further comprises a fluid reservoir assembly in communication with the lumen and operable to exert a pressure on the diaphragm, wherein the pressure is operable to move the diaphragm from the closed diaphragm configuration to the open diaphragm configuration.

17. The method of claim 15 further comprising activating the vacuum generation device such that a continuous vacuum pressure is exerted on the diaphragm.

18. The method of claim 15 further comprising cycling the diaphragm between the open diaphragm configuration and the closed diaphragm configuration.

19. The method of claim 15 further comprising cycling the diaphragm between the open diaphragm configuration and the closed diaphragm configuration at a predetermined time interval.

20. The method of claim 15 further comprising macerating the material from the subject with the diaphragm.

\* \* \* \* \*